US009121050B2

United States Patent
Franciskovich et al.

(10) Patent No.: US 9,121,050 B2
(45) Date of Patent: Sep. 1, 2015

(54) NON-ENZYME BASED DETECTION METHOD FOR ELECTRONIC MONITORING OF BIOLOGICAL INDICATOR

(71) Applicant: American Sterilizer Company, Mentor, OH (US)

(72) Inventors: Phillip P. Franciskovich, Concord, OH (US); Tricia A. Cregger, Fairlawn, OH (US)

(73) Assignee: American Sterilizer Company, Mentor, OH (US)

( * ) Notice: Subject to any disclaimer, the term of this patent is extended or adjusted under 35 U.S.C. 154(b) by 438 days.

(21) Appl. No.: 13/836,787

(22) Filed: Mar. 15, 2013

(65) Prior Publication Data

US 2014/0262829 A1  Sep. 18, 2014

(51) Int. Cl.
*G01N 27/00* (2006.01)
*C12Q 1/22* (2006.01)
*C12Q 1/00* (2006.01)
*C12Q 1/68* (2006.01)

(52) U.S. Cl.
CPC ........... *C12Q 1/22* (2013.01); *B01L 2300/0609* (2013.01); *B01L 2300/0816* (2013.01); *C12Q 1/001* (2013.01); *C12Q 1/006* (2013.01); *C12Q 1/6816* (2013.01); *C12Q 2527/125* (2013.01)

(58) Field of Classification Search
CPC ........ C12Q 1/6816; C12Q 1/006; C12Q 1/22; C12Q 2527/125; C12Q 1/001; B01L 2300/0609; B01L 2300/0816
See application file for complete search history.

(56) References Cited

U.S. PATENT DOCUMENTS

| | | | |
|---|---|---|---|
| 4,927,516 | A | 5/1990 | Yamaguchi et al. |
| 5,413,690 | A | 5/1995 | Kost et al. |
| 5,789,255 | A | 8/1998 | Yu |
| 5,843,692 | A | 12/1998 | Phillips et al. |
| 5,902,731 | A | 5/1999 | Ouyang et al. |
| 6,077,660 | A | 6/2000 | Wong et al. |
| 6,102,872 | A | 8/2000 | Doneen et al. |
| 6,168,957 | B1 | 1/2001 | Matzinger et al. |

(Continued)

FOREIGN PATENT DOCUMENTS

| | | |
|---|---|---|
| WO | 0210708 | 2/2002 |
| WO | 2008082728 | 7/2008 |
| WO | 2012012055 | 1/2012 |

OTHER PUBLICATIONS

PCT/US2014/017909; PCT International Search Report and Written Opinion of the International Searching Authority dated Jun. 2, 2014.

*Primary Examiner* — Dennis M White
(74) *Attorney, Agent, or Firm* — Renner, Otto, Boisselle & Sklar, LLP (57) ABSTRACT

A sterilization indicator system and method of using the system to determine efficacy of a sterilization process. The system may include a vial having an optional first compartment and a second compartment comprising a growth medium comprising one or more of a disaccharide, an oligosaccharide or a polysaccharide capable of conversion to a monosaccharide by germinating spores of the one or more species of microorganism, the vial being free of the monosaccharide prior to use; a strip including two or more electrodes to oxidize the monosaccharide and to carry a resulting electrical signal, and an apparatus to detect and measure the electrical signal resulting from the oxidation. Spores of a suitable biological indicator may be disposed in the first compartment and/or on the strip.

14 Claims, 5 Drawing Sheets

(56) References Cited

U.S. PATENT DOCUMENTS

| | | | |
|---|---|---|---|
| 6,193,873 B1 | 2/2001 | Ohara et al. |
| 6,268,162 B1 | 7/2001 | Phillips et al. |
| 6,270,637 B1 | 8/2001 | Crismore et al. |
| 6,338,790 B1 | 1/2002 | Feldman et al. |
| 6,531,322 B1 | 3/2003 | Jurik et al. |
| 6,555,061 B1 | 4/2003 | Leong et al. |
| 6,562,625 B2 | 5/2003 | Modzelewski et al. |
| 6,572,822 B2 | 6/2003 | Jurik et al. |
| 6,716,577 B1 | 4/2004 | Yu et al. |
| 6,723,500 B2 | 4/2004 | Yu |
| 6,818,180 B2 | 11/2004 | Douglas et al. |
| 6,855,243 B2 | 2/2005 | Khan |
| 6,858,401 B2 | 2/2005 | Phillips et al. |
| 6,881,551 B2 | 4/2005 | Heller et al. |
| 6,989,243 B2 | 1/2006 | Yani et al. |
| 6,990,367 B2 | 1/2006 | Kiser et al. |
| 6,998,248 B2 | 2/2006 | Yani et al. |
| 7,226,978 B2 | 6/2007 | Tapsak et al. |
| 7,244,394 B2 | 7/2007 | Carney et al. |
| 7,288,174 B2 | 10/2007 | Cui et al. |
| 7,429,462 B2 | 9/2008 | Morris et al. |
| 7,548,772 B2 | 6/2009 | Shartle et al. |
| 7,549,323 B2 | 6/2009 | Charlton et al. |
| 7,653,492 B2 | 1/2010 | Davies et al. |
| 7,655,119 B2 | 2/2010 | Davies |
| 7,711,402 B2 | 5/2010 | Shults et al. |
| 7,731,835 B2 | 6/2010 | Buck et al. |
| 7,740,801 B2 | 6/2010 | Saini et al. |
| 7,835,777 B2 | 11/2010 | Shults et al. |
| 7,860,545 B2 | 12/2010 | Shults et al. |
| 7,875,461 B2 | 1/2011 | Docherty et al. |
| 7,888,292 B2 | 2/2011 | Bock et al. |
| 7,909,984 B2 | 3/2011 | Heller et al. |
| 7,922,985 B2 | 4/2011 | Mahoney et al. |
| 7,943,022 B2 | 5/2011 | Teodorczyk et al. |
| 7,964,372 B2 | 6/2011 | Marfurt |
| 7,964,390 B2 | 6/2011 | Rozakis et al. |
| 7,974,672 B2 | 7/2011 | Shults et al. |
| RE42,953 E | 11/2011 | Crismore et al. |
| 8,105,244 B2 | 1/2012 | Ghesquiere et al. |
| 8,133,178 B2 | 3/2012 | Brauker et al. |
| 8,142,642 B2 | 3/2012 | Heller et al. |
| 8,155,723 B2 | 4/2012 | Shults et al. |
| 8,178,313 B2 | 5/2012 | Mahoney et al. |
| 8,182,671 B2 | 5/2012 | Feldman et al. |
| 2004/0028557 A1 | 2/2004 | Leong et al. |
| 2007/0208243 A1 | 9/2007 | Gabriel et al. |
| 2008/0057528 A1 | 3/2008 | Sayre et al. |
| 2008/0177166 A1 | 7/2008 | Pronovost et al. |
| 2008/0281178 A1 | 11/2008 | Chuang et al. |
| 2009/0184004 A1 | 7/2009 | Chatelier et al. |
| 2009/0270704 A1 | 10/2009 | Peyser et al. |
| 2010/0126884 A1 | 5/2010 | Wang et al. |
| 2010/0204559 A1 | 8/2010 | Shults et al. |
| 2010/0216175 A1 | 8/2010 | Melker et al. |
| 2010/0259747 A1 | 10/2010 | Sekimoto |
| 2010/0270152 A1 | 10/2010 | Cardosi et al. |
| 2010/0273249 A1 | 10/2010 | Cardosi et al. |
| 2010/0298679 A1 | 11/2010 | Wu et al. |
| 2011/0040163 A1 | 2/2011 | Telson et al. |
| 2011/0048972 A1 | 3/2011 | Moffat et al. |
| 2011/0155585 A1 | 6/2011 | Chatelier et al. |
| 2011/0281287 A1 | 11/2011 | Marfurt |
| 2011/0290668 A1 | 12/2011 | Moffat et al. |
| 2011/0309846 A1 | 12/2011 | Elder et al. |
| 2011/0311711 A1 | 12/2011 | Say et al. |
| 2011/0319734 A1 | 12/2011 | Gottlieb et al. |
| 2012/0037514 A1 | 2/2012 | Wu et al. |
| 2012/0043204 A1 | 2/2012 | Young et al. |
| 2012/0073986 A1 | 3/2012 | Jackson et al. |
| 2012/0097554 A1 | 4/2012 | Shah et al. |

NON-ENZYME BASED DETECTION METHOD FOR ELECTRONIC MONITORING OF BIOLOGICAL INDICATOR

TECHNICAL FIELD

The present invention relates to biological indicators for testing the efficacy of sterilization processes, more specifically, to non-enzyme-based methods for monitoring such biological indicators, in which such monitoring can be carried out electronically.

BACKGROUND

One of the most important classes of indicators are the biological indicators (BI). Biological indicators provide the highest degree of assurance that sterilization conditions were met within the processor or processed load itself. This type of indicator is meant to represent the worst case for the processing system by providing an extremely high number of highly resistant organisms to that particular process within or on the indicator. Usually bacterial spores are the organism of choice for monitoring sterilization systems.

Biological indicators typically consist of microorganisms inoculated onto a carrier material. The microorganisms are typically bacterial spores that are known to be very resistant to the particular sterilization medium in which they are to be used. The carrier is placed into a sterilization cycle along with the medical device load. Following completion of the cycle the biological indicator is incubated and monitored for growth for up to seven days. Growth of a biological indicator indicates that the sterilization process was not adequate to attain complete sterilization and that the medical device load needs to be reprocessed before use. No growth of a biological indicator confirms that conditions within the sterilizer were adequate to kill at least the number of bacterial spores loaded onto the indicator (e.g., 10 bacterial spores) and therefore provides a level of assurance that the medical device load is sterile. Unfortunately many medical devices are actually used prior to the user knowing the results of the full incubation. Thus, there is a need in the hospital setting for detection of viable biological indicator spores in the shortest possible timeframe.

Historically, the detection of viable biological indicators relied on visual means of detection. The growth and multiplication of viable organisms can be seen/detected as evidenced by turbidity in the growth media. This turbidity can take days to become noticeable. Another visual and more common means of detection is with a colorimetric pH indicator. As viable organisms begin to metabolize and use up the nutrient sources such as sugars that are provided in the growth media, they excrete acidic waste products. As these acidic waste products accumulate in the growth media, the pH of the system is lowered resulting in a color change of the growth media if a pH indicator is present. Detection by this means usually takes 18-48 hours.

More recently, fluorescence has been used to detect the activity of enzymes that are produced by the organisms of interest by adding a fluorogenic enzymatic substrate to the growth media. This newer methodology lessens the incubation time from days to hours. However, the main limitation for reducing the incubation time beyond that seen for the fluorescence methodology is the inherent background fluorescence that naturally occurs with many components of the biological indicator including the plastic vials and growth media. Authentic, detectable signals must be high enough to be distinguishable over this inherent native background fluorescence. Therefore to increase the sensitivity of the system one needs to either reduce the background fluorescence (noise) or move to a different technology that has higher sensitivity (signal).

Thus, in the prior and current art, biological indicators rely on colorimetric or fluorometric means to determine viability. Detection is limited by the need for the generated signals, whether colorimetric or fluorometric, to be above substantial background levels. This has resulted in detection times for viable organisms on the order of hours to days in order for sufficient signal to be accumulated to be detectable above background levels. It would be beneficial for both hospitals and patients for the detection time of viable organisms in biological indicators to be on the order of minutes or less.

SUMMARY

One such method that permits control over the signal to noise ratio is electrical detection. The monitoring of changes in the electrical properties of systems is a sensitive means to monitor for other changes within that system. The resulting electric outputs can then be conditioned by electronic means to provide amplified and filtered signals that are directly proportional to the reagent generating them.

The present invention provides a rapid detection of viable microorganisms of a biological indicator using a non-enzyme-based electronic detection method to detect the accumulation of simple sugars such as glucose resulting from the enzymatic breakdown of complex sugars. The non-enzyme-based system of the present invention includes a combination of at least one naturally occurring glycosidase present in a viable spore and electrodes adapted to oxidize a simple sugar, such as glucose, produced by the glycosidase in the viable spore. The incubation or growth medium provided for the spores post-sterilization is provided free of the simple sugar and with a complex sugar, such as a disaccharide or a polysaccharide. The glycosidase reacts with the complex sugar added to the growth media and breaks it down into the simple sugars, including, for example, at least one glucose. The simple sugar product is then exposed to the electrodes on a strip that are adapted to selectively oxidize glucose which produces an electron transfer as part of its oxidation of the simple sugar. The quantity of the electron transfer is proportional to the amount of the simple sugar produced by viable spores. The transfer of free electrons in the oxidation can be monitored and measured electronically. If the electronic monitoring detects electron transfer, it means that at least some spores are viable and have survived the sterilization process, and so showing the sterilization was not efficacious. The electrodes may be those used in standard, state of the art blood glucose monitoring devices, and in fact, known state of the art blood glucose monitoring devices can be readily adapted for use in determining the presence of any glucose or simple sugar in the combined media. Thus, the present invention allows the determination of the efficacy of the sterilization process by a very specific, very sensitive method that can be simply carried out and measured electronically. In one embodiment, the system and process uses standard, state of the art devices designed for use in monitoring blood glucose levels in diabetic patients.

Thus, in one embodiment, the present invention relates to a sterilization indicator system, including:

spores of one or more species of microorganism;

a vial comprising an optional first compartment and a second compartment containing a growth medium comprising one or more of a disaccharide or a polysaccharide capable of conversion to a monosaccharide by germinating spores of the one or more species of microorganism, the vial being adapted to combine contents of the second compartment with the spores for analysis after the vial has been exposed to the sterilant;

a strip comprising two or more electrodes adapted to oxidize the monosaccharide and to carry an electrical signal resulting from the oxidation of the monosaccharide, wherein the two or more electrodes are adapted to provide contact with the combined contents of the second compartment and the spores during and/or after incubation; and an apparatus linked or linkable to the two or more electrodes and adapted to detect and measure the electrical signal resulting from electron transfer when the monosaccharide is oxidized by the two or more electrodes, wherein the system is free of the monosaccharide prior to exposure to a sterilant.

In one embodiment, the first compartment is absent, the spores are disposed on the strip, and the strip initially is separate from the second compartment.

In one embodiment, the first compartment is present, the spores are disposed on the strip, and the strip initially is separate from both the first compartment and the second compartment.

In one embodiment, the first compartment is present, the spores are disposed in the first compartment, and the strip initially is separate from both the first compartment and the second compartment.

In one embodiment, the first compartment is present, the spores are disposed in the first compartment, and the strip initially is in the first compartment.

In one embodiment, the first compartment is present, the spores are disposed on the strip, and the strip initially is in the first compartment.

In one embodiment, the first compartment is present, the spores are disposed in the first compartment, and the strip initially is in the second compartment.

In one embodiment, the monosaccharide is glucose.

In one embodiment, the one or more species of microorganism comprises one or both of *Geobacillus stearothermophilus* and *Bacillus atrophaeus*.

In one embodiment, the apparatus is a glucose reader.

In one embodiment, the two or more electrodes are linkable to a glucose reader by a wireless link.

In one embodiment, the disaccharide is maltose that is converted to glucose by a glucosidase produced by or present in the germinating spores.

In one embodiment, the at least two electrodes comprise graphite, graphene, carbon, carbon nanotubes, gold, platinum, palladium, silver, nickel or copper or a combination or alloy of any two or more thereof.

Thus, the present invention provides an elegant and simple solution to the problem of rapidly determining the efficacy of a sterilization process, and provides an apparatus specially adapted for such use.

BRIEF DESCRIPTION OF THE DRAWINGS

The present invention may be useful with a variety of sterilization apparatus. The annexed drawings are intended to provide an exemplary, non-limiting depiction of a suitable sterilization apparatus and to demonstrate the disclosed process, for the purpose of providing a better understanding of the invention, and are not intended to be limiting in any way. In the annexed drawings, like parts and features may have like references.

It should be appreciated that for simplicity and clarity of illustration, elements shown in the Figures have not necessarily been drawn to scale. For example, the dimensions of some of the elements may be exaggerated relative to each other for clarity. Further, where considered appropriate, reference numerals have been repeated among the Figures to indicate corresponding elements.

Furthermore, it should be appreciated that the process steps and structures described below may not form a complete process flow for producing an end-useable sterilization indicator. The present invention can be practiced in conjunction with apparatus and processing techniques currently used in the art, and only so much of the commonly practiced process steps are included as are necessary for an understanding of the present invention.

DETAILED DESCRIPTION

The biological indicators described in the following rely on a new mechanism to detect spore viability. The invention described here utilizes an electronic signal that is generated based on the accumulation of a monosaccharide, e.g., glucose, that results from the ability of viable organisms to break down complex sugars. Electronic detection methods based on glucose have been readily available for years for monitoring the glucose levels in the blood of diabetic patients. Until now, however, there has been neither use of nor suggestion to adapt these electronic detection mechanisms as a means to detect viable organisms following sterilization processes.

Most organisms have inherent capabilities to break down complex sugars (such as maltose) into simple sugars (such as glucose) in order that the more useful simple sugar molecule can be utilized as an energy source by the organism. The same basic reactions utilized in monitoring glucose levels in blood can be adapted to detect viable organisms, such as spores, that may survive a sterilization cycle. In one embodiment of the present invention, the same electronic glucose monitors may be adapted for use in monitoring efficacy of sterilization processes. Unlike blood glucose monitoring, however, where glucose is prevalent and is measured directly, in the present invention, initially no glucose is present, and glucose is only obtained from an undetectable complex carbohydrate molecule that must first be acted upon by a viable organism before glucose is released and able to be detected. If no viable organisms survive the sterilization conditions, there is no glucose at all present to be detected. Thus, in the present invention, the simple sugar, usually glucose, is never present unless and until a viable microorganism that has survived the sterilization conditions being monitored breaks down a complex carbohydrate to form the simple sugar. If and when this breakdown occurs, it may be detected and measured in accordance with the present invention.

As viable spores begin to germinate (a fundamental life activity) they produce and release enzymes that enable them to break down the complex sugars into more readily usable simple sugars such as glucose. By formulating a medium that is high in complex sugars, such as disaccharides, oligosaccharides and/or polysaccharides (selected on the basis that they can be broken down by the active enzymes of viable test organisms selected for the sterilization indicator) an increase in monosaccharide, e.g., glucose, would be expected upon exposing viable spores to this medium and this increasing concentration of the monosaccharide in the growth media can be detected electronically by electrodes adapted to oxidize the monosaccharides. Under the conditions of sterilization, spores are killed and any enzymes the spores may have possessed prior to the sterilization will be destroyed. Therefore, an increase in the monosaccharide detected after exposure of these spores to the medium of this invention means that the organisms are viable (proof of life). The spore mediated conversion of complex sugars to glucose represents the first step in detecting viable organisms according to the process of the present invention. The second step is the oxidation of any thus-produced monosaccharide by the two or more electrodes, and the third step is detection of any electrical signal accompanying the oxidation.

The organisms of most interest for monitoring sterilization processes are *Geobacillus stearothermophilus* and *Bacillus atrophaeus*. Germinating spores of both organisms produce enzymes, including, for example, alpha-glucosidase, which can break down the complex sugar maltose into two glucose molecules. This exemplifies just one means to achieve the first step in the present invention. Other spore produced enzymes may also be used to break down other complex sugars, e.g., disaccharides, oligosaccharides or polysaccharides, to produce monosaccharides such as glucose.

The monosaccharide, e.g., glucose, can then be oxidized by the electrodes to achieve the second step in the present invention. The monosaccharide may be detected by non-enzymatic glucose biosensors using, for example, a fixed potential, chronoamperometric method for the direct electrochemical determination of newly formed monosaccharide molecules. Suitable sweeping potential methods are known to those skilled in the art. For example, C. Fang, C. Yi, Y. Wang, Y. Cao and X. Liu, in *Biosens. Bioelectron.* 24 (2009) 3164 disclose a molecularly imprinted polymer that can be used. Other methods of detection by non-enzymatic glucose biosensors are known in the art as well.

Thus the process is dependent upon the first step in the process, in which any germinating spores produce an enzyme capable of breaking down complex carbohydrates, e.g., maltose or lactose, to more simple sugars, e.g., glucose. Failure to achieve production of the end product of the first step (as will be the case if the spores are killed) prevents detection of the simple sugar in the second step. So, in the absence of any product of the first reaction (e.g., glucose converted from maltose) no signal will result or be observed. In this case, absence of any signal derived from oxidation of a monosaccharide such as glucose would mean the monitored sterilization was successful.

Examples of suitable disaccharides are maltose, lactose, sucrose, trehalose, cellobiose, and isomaltose Examples of suitable oligosaccharides are fructo-oligosaccharides, galacto-oligosaccharides, mannan-oligosaccharides, gum arabic, guar gum and guar hydrolysate.

Examples of suitable polysaccharides are starch, dextrin, glycogen, cellulose and pectin. Other possibly suitable polysaccharides include gellan, Gum ghatti, karaya, tragacanth, psyllium seed, xanthan, guar, ivory nut mannan, konjac, locust bean, tamarind, tara, carrageenans, alginates, fucoidans, laminarin, agar, pullulan, welan and scleroglucan.

Other suitable disaccharides, oligosaccharides and/or polysaccharides may be known to those of skill in the art, and may also be useful with the present invention.

The present invention utilizes an electronic signal that relies on detecting the emergence of simple sugars that are generated from the breakdown of complex sugars when in the presence of germinating spores of indicator organisms. Electronic detection methods based on sugars have been readily available for years for monitoring the glucose levels in the blood of diabetic patients. Until now, however, these electronic detection mechanisms have not been used or suggested for use as a means to detect viable organisms following sterilization processes. It is enabled here by the realization that conditions can be set so that in the absence of viable, surviving spores, no monosaccharide, e.g., glucose, is present in the system and none will be detected, while at the same time providing a very sensitive measurement of any of the monosaccharide that does become present due to the presence of germinating spores. The present invention thus takes advantage of the fact that most living organisms have inherent capabilities to break down complex sugars (such as maltose) into simple sugars (such as glucose) in order that the more useful glucose molecule can be utilized as an energy source by the organism. Glucose monitoring through enzyme-based electronic detection methods (e.g. glucose oxidase based biosensors) have been readily available for years to monitor the glucose levels in the blood of diabetic patients. These same basic methods for monitoring glucose levels in blood can be altered and adapted to detect viable organisms, such as spores, that may survive a sterilization cycle. As viable spores begin to germinate, they produce enzymes that enable them to break down complex sugars into more readily usable simple sugars such as glucose. By formulating a medium that is high in complex sugars (selected on the basis that they can be broken down by the active enzymes of viable selected organisms), an increase in glucose would be expected upon exposing viable spores to this medium and incubating. Under the conditions of sterilization, spores are killed and any of the spore derived enzymes it may already possess will be destroyed.

Therefore, an increase in glucose detected after exposure of these spores to this medium confirms that the organisms are viable. The germinating-spore-mediated conversion of complex sugars into simple sugars is directly detected in the electrocatalytic process of the present invention. This provides a heretofore unavailable method for the detection of viable indicator spores without the requirements for exogenously added enzyme or any added signal generating chemicals.

Thus, in one embodiment, the present invention relates to a sterilization indicator system, including spores of one or more species of microorganism; a vial comprising an optional first compartment and a second compartment containing a growth medium comprising one or more of a disaccharide, an oligosaccharide or a polysaccharide capable of conversion to a monosaccharide by germinating spores of the one or more species of microorganism, the vial being adapted to combine contents of the second compartment with the spores for analysis after the vial has been exposed to a sterilant; a strip comprising two or more electrodes adapted to oxidize the monosaccharide and to carry an electrical signal resulting from the oxidation of the monosaccharide, wherein the two or more electrodes are adapted to provide contact with the combined contents of the second compartment and the spores during and/or after incubation; and an apparatus linked or linkable to the two or more electrodes and adapted to detect and measure the electrical signal resulting from electron transfer when the monosaccharide is oxidized by the two or more electrodes, in which the system is free of the monosaccharide prior to exposure to the sterilant. Since the system is free of the monosaccharide prior to exposure to the sterilant, any electrical signal which is detected and measured would indicate the presence of viable, germinating spores, and this would then indicate that the sterilization process failed to fully sterilize the load, since the indicator contained surviving spores.

The electrodes suitable for use with the present invention include a variety of electrode types, sensitivities, linear ranges, limits of detection and suitability for deposition by Inkjet, silk screen or similar methods. The composition and physical form of these electrodes define them as electrocatalysts and include, but are not limited to: porous or intercalated layers (e.g. comprising one or more of copper, nickel, silver, platinum and gold), graphite, graphene, carbon, carbon nanotubes, nanoparticles (e.g. comprising for example copper and carbon nanotubes, doped platinum and metal films), unmodified metals such as copper, nickel, silver, platinum and gold, chemically modified electrodes, alloys (e.g., nickel-titanium, nickel-copper and nickel-chromium-iron), electrochemically deposited forms such as (e.g., copper oxides and bimetallic gold/copper) and polymers and composites (e.g., polymeric nickel-oxide and gold/Nafion®). Reported sensitivities range from $2\times10^{-4}$ to over 200 mA per mM (milliamp per millimole) and the linear ranges are as high as 4 to 5 orders of magnitude. Limits of detection can be achieved as low as $2\times10^{-8}$ mM. Though many of these physical-electric properties are far below what is needed of blood glucose determination, they are ideally suited for monitoring glucose generation in the presence of a small number of surviving indicator spores.

Non-enzymatic glucose sensors can be operated using, for example sweeping potential methods such as linear sweep, and cyclic and square wave voltammetry. The process of non-enzymatic electrocatalysis occurs when the analyte (e.g., newly emergent glucose) adsorbs to the electrode surface forming a bond which alternately adsorbs and desorbs catalyzing the oxidation of glucose and inducing the transfer of electrons. It is this flow of energy which is proportional to the quantity of glucose in the system and is thus the means by which the presence of viable spores may be detected.

The following exemplary reactions depict functions of the enzyme naturally occurring in any germinating spores that survive the sterilization process, and of the oxidation by the electrodes in the strip added to the incubation/recovery medium in accordance with an embodiment of the present invention in which maltose is the complex sugar (disaccharide) and glucose is the simple sugar or monosaccharide:

When a voltage differential is applied across a working electrode and a reference electrode, the working electrode becomes polarized and an oxidizing current resulting from the electron transfer is produced. This oxidizing current can be measured and is proportional to the amount of simple sugar present is the system after the sterilization and incubation, when none was present prior to the sterilization and incubation.

This invention utilizes organisms that are resistant to the sterilization process to be monitored in conjunction with a specialized medium that has been formulated with complex sugars, e.g., disaccharides, oligosaccharides and/or polysaccharides that can be reduced by viable spores to monosaccharides such as the simple sugar glucose. The increases in the simple sugar levels in the system if viable spores are present can thus be monitored electronically.

In one embodiment, the at least two electrodes comprise graphite, graphene, carbon, carbon nanotubes, gold, platinum, palladium, silver, nickel or copper or a combination or alloy of any two or more thereof. Other suitable electrode materials, as known in the blood glucose monitoring arts, can be used, as will be understood by the skilled person.

As used herein, the phrases "an electrical signal resulting from the oxidation of the monosaccharide", and "an electrical signal resulting from the oxidation of the glucose" mean that the electrical signal is that signal which results from the oxidation, as compared to a background signal, such as might be provided by use of a reference electrode. Thus, while there may be some threshold electrical signal between the electrodes, even in the absence of the oxidation, it is the signal resulting from the oxidation that is of interest and is measured in the present invention.

Figure 1:
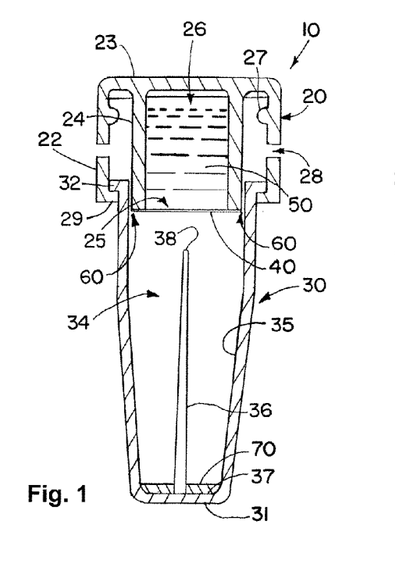
FIG. 1 is a schematic cross-sectional view of a first embodiment of a sterilization indicator suitable for use with embodiments of the present invention, in a pre-activated configuration.
Figure 2:
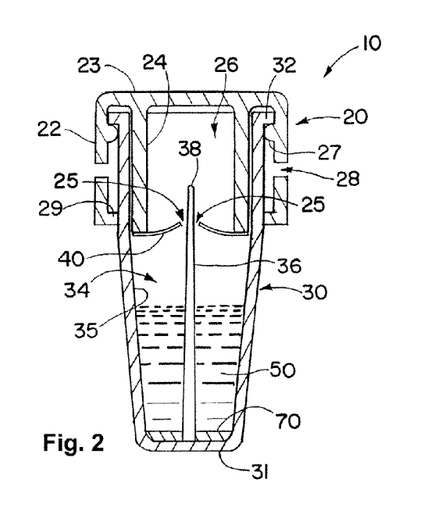
FIG. 2 is a schematic cross-sectional view of the sterilization indicator of FIG. 1 in an activated configuration.

Referring now to the drawings, FIGS. 1 and 2 show a sterilization indicator system 10 useful with a first exemplary embodiment of the present invention. The following descriptions are provided to generally inform how an exemplary sterilization system works, and are not intended to limit the invention. The indicator system 10 comprises a cap 20 that is mountable on a container 30. The container 30 includes a closed, bottom end 31 and an open, upper end, and defines an interior space 34. The cap 20 has an outer wall 22, an open, lower end, and a closed, upper end 23. The cap also includes an inner wall (or walls) 24 disposed interior of the cap's outer wall, forming a separate wall, and defining an inner chamber 26. The inner chamber 26 includes an opening 25 adjacent to the bottom end of the wall(s) 24. The chamber 26 contains a fluid 50, and the cap 20 includes a breakable barrier 40 disposed about the opening 25 of the chamber 26 to encapsulate the fluid 50 within the chamber 26.

In the embodiment illustrated in FIGS. 1 and 2, the indicator system is configured for the cap 20 to be mounted to the container 30 in a snap-fit relationship. In other embodiments, not shown, the indicator system may be configured for the cap to be mounted to the container in a threaded relationship in which the cap is engaged with the container by threads and the system is activated by rotating the cap with respect to the container, i.e., by screwing the cap further onto the container. As shown in FIGS. 1 and 2, the container 30 includes an annular projection 32 forming a ridge or lip adjacent or near the upper end of the container. The cap 20 includes an annular projection 29 forming a ridge or lip adjacent the bottom of the cap. The cap 20 may be mounted onto the container 30 by sliding the ridge 29 of the cap over the ridge 32 of the container. The ridge 32 of the container 30 engages the ridge 29 on the cap 20 to prevent the cap 20 and container 30 from decoupling. The cap 20 and container 30 may be sized such that the ridge 32 exerts a sufficient amount of pressure against the cap 20 to prevent the cap 20 from sliding downward without applying an external downward force to the cap 20. In this way, the breakable barrier 40 may be kept spaced apart from the edges 38 of puncture members 36 so the breakable barrier 40 does not contact and/or is not broken by the puncture members until such time as desired to activate the indicator.

As shown in FIGS. 1 and 2, the container 30 is adapted to break the breakable barrier 40. The containers include one or more projections 36 (which may also be referred to herein as "puncture members") having an edge 38 adapted to break or puncture the breakable barrier 40 when the cap 20 with the breakable barrier 40 is moved downward toward and the barrier 40 contacts the edge 38 of projection 36. The puncture member 36 is shown as being integral with and extending up from the bottom wall 37 of the container. In another embodiment, not shown, puncture members 36 may extend both from the side wall 35 and from the bottom wall 37.

To evaluate a sterilization process, a calibrated concentration of microorganisms is disposed within the interior 34 of the container 30. The microorganisms may be disposed directly on the walls 35 of the container or may be provided on a support member (e.g., support member 70) that is disposed within the container 30 or on electrodes that may be variously located, as described below with respect to FIGS. 6-11. The sterilization indicator is then assembled by mounting the recovery medium-filled cap 20 on the container 30. The cap 20 may be mounted by snap-fitting the cap 20 onto the container 30 as described above, or, for example, by a threaded mounting. With reference to FIG. 1, the recovery medium-filled cap 20 is mounted on the container 30 in a first, non-activated (or open) position such that the breakable barrier 40 remains intact and is not punctured by the puncture members 36. Desirably, in the first, non-activated position, the breakable barrier 40 is positioned away from and does not contact the edges 38 of the puncture members 36.

With the indicator 10 assembled such as shown in FIG. 1, the sterilization indicator then can be subjected to a sterilization process. The cap 20 is shown as having apertures 28 through which a sterilant vapor may enter and flow into indicator system. The sterilant enters the cap through the apertures 28 (into the space between the outer wall 22 and the inner wall 24) and flows into the container 30 through a space 60 defined between the exterior surface of the inner wall 24 on the cap 20 and the inner surface of the wall 35 on the container 30. The sterilant vapor flows into the container 30 and acts upon the microorganisms of the biological indicator, in this embodiment.

After the sterilization process is completed, the sterilization indicator may be activated by moving the cap 20 downward toward the container 30 to a second (or closed or activated) position, which is illustrated in FIG. 2. The cap 20 is moved downward by applying a sufficient downward force or pressure on the cap 20. As the cap 20 is moved downward, the breakable barrier 40 is brought into contact with the edge 38 of the puncture member 36, and eventually moved into a position such that the edge 38 of the puncture member 36 punctures or penetrates the breakable barrier 40. When the breakable barrier 40 is punctured, the opening 25 of the chamber 26 is exposed, and the liquid recovery medium 50 drains into the interior region 34 of the container 30 and into contact with the microorganisms as shown in FIG. 2.

As shown in FIGS. 1 and 2, in this embodiment, the inner surface of the cap 20 includes a second annular projection 27, and the cap may be moved downward to a position such that the upper portion of the projection 27 engages the bottom of ridge 32 on the container 30, and the cap 20 is held in the second, closed/activated position. The second, closed/activated position may serve to hold the cap 20 in a sealed relationship with the container 30, which may prevent additional microorganisms from entering the system. Use of the projections 27 is optional, in other embodiments of the sterilization system. U.S. Pat. No. 5,770,393 illustrates other suitable configurations, and this patent is incorporated herein by reference for its teachings relating to configurations of cap and container. In another alternative embodiment, the inner surface of the cap 20 and the outer surface of the container 30 may be threaded, and the cap 20 may be moved into and maintained in a closed position by screwing the cap 20 onto the container 30, in which the cap 20 may be threaded as shown, e.g., in U.S. Pat. No. 8,173,388 B2, which may be consulted for additional details on this embodiment of the vial, and which is hereby incorporated herein by reference for its teachings relating to the vial and cap configuration of this and the foregoing embodiments. All of these alternative configurations are within the scope of the present invention.

As described above, the cap 20 in the embodiment illustrated in FIGS. 1 and 2 is shown as having the aperture 28 to allow for the ingress of the vapor sterilant into the indicator. It will be appreciated, however, that the cap need not be provided with such a feature. The number, size, shape, and/or location of the aperture(s) may be selected as desired, with consideration of the particular sterilant with which the sterilization indicator is to be used. For example, the location, shape, and size of the apertures in the cap and/or the container may be selected to provide a tortuous path for the entrance and exit of the sterilization vapor between the microorganisms and the surrounding environments. The tortuous path may also serve to inhibit or prevent contamination from external agents, and to make certain that an adequate amount of sterilant is available. By including the tortuous path, it is more likely that the entire load will be exposed to the sterilant thereby killing any extant microorganisms before the test organism in the sterilization indicator is killed.

Apertures may be provided in the container in addition to or as an alternative to providing apertures in the cap. If apertures are not provided in the cap, the inner wall(s) need not be located to provide a space between the inner wall of the cap and the inner surface of the container. Additionally, if apertures are provided in the container, they should be located such that the growth medium does not leak or spill out through such apertures when the indicator is activated and the barrier is broken.

Figure 3:
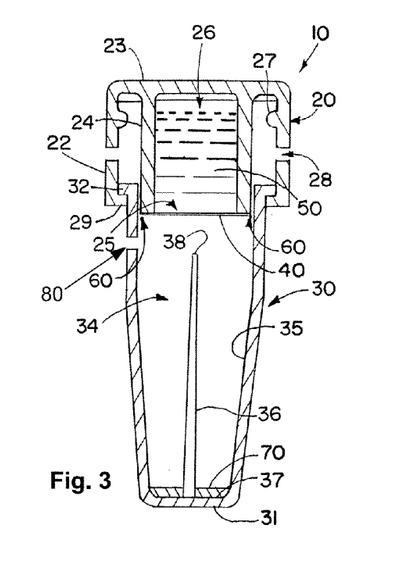
FIG. 3 is a schematic cross-sectional view of a second embodiment of a sterilization indicator suitable for use with embodiments of the present invention, in pre-activated configuration, similar to that of FIG. 1.

FIG. 3 depicts an indicator 10 in which an aperture 80 is formed in the sidewall 35 of the container 30 at an appropriate position, in addition to the apertures 28 in the cap 20. The aperture shown in FIG. 3 is in the sidewall 35 of the container 30 be near the top of the container 30, in the vicinity of the edge 38 of the puncture member 36, to avoid leakage or spilling after activation. As can be seen from FIG. 3, after activation, the aperture 80 at this location will be covered by the cap 20 in the activated position. It is noted that the indicator 10 shown in FIG. 3 includes the aperture 28 in the cap 20, but this is not necessary. In one embodiment (not shown), the container 30 includes the aperture 80 and is used with a cap similar to the cap 20, but which does not include an aperture such as the aperture 28. Thus, an aperture can be provided either in the cap or in the container, or in both the cap and the container.

After the sterilization process has been completed, the cap 20 is pressed or twisted downward such that the edge 38 of the puncture member 36 penetrates and breaks the breakable barrier 40 releasing the growth medium in the space 26 to mix with and incubate with any of the biological indicator microorganisms that may have survived the sterilization process. The recovery medium 50 may comprise an aqueous medium or aqueous solution that provides for germination, metabolism and subsequent grow out of organisms as required. The aqueous medium or aqueous solution may be buffered.

The sterilization indicator 10 is then incubated for a sufficient period of time to allow microorganism viability to be determined. During incubation, any viable microorganisms will begin to metabolize and germinate, and this metabolism and germination includes activity by the enzymes to break down the disaccharide. oligosaccharide or polysaccharide to produce a monosaccharide, for example to break down maltose to produce glucose. In accordance with the present invention, the glucose "byproduct" is then available to be oxidized by the electrodes that are provided, which oxidation is detected via the electrical signal produced by the two or more electrodes described herein.

Figure 4:
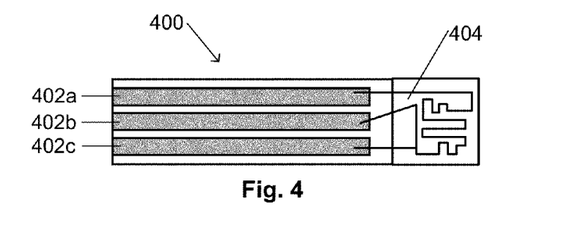
FIG. 4 is a schematic depiction of an electro-conductive strip containing three electrodes suitable for use in an embodiment of the present invention.

FIG. 4 is a schematic depiction of an electro-conductive strip 400 containing three electrodes 402a, 402b and 402c suitable for use in an embodiment of the present invention. The strip 400 further includes electronics 404 adapted to provide electrical communication between the electrodes 402a, 402b and 402c, and an apparatus linked or linkable to the electrodes that is adapted to detect and measure the electrical signals resulting from electron transfer when any glucose present is oxidized by the electrodes. As disclosed and described, the electrodes 402a, 402b and 402c are capable of acting upon a monosaccharide, such as glucose, to oxidize the monosaccharide and produce a detectable electron transfer.

As described, the at least two electrodes, may include two electrodes that participate in the oxidation, while the third electrode may function as a reference electrode. Other embodiments, not shown, may include a different number of electrodes. For example, the reference electrode may be omitted, or an additional electrode or pair of electrodes may be added. The electronics 404 may include any appropriate electrical connection between the electrodes and an external apparatus that detects and measures any electrical signals generated. Such connections may include, but are not limited to, hard wiring, physical electrical contacts, e.g., spring-loaded or jacks, Ethernet, Bluetooth, 802.11, wireless local area networks (WLANs), WiFi, WiMax and the like, or any other wired or wireless communication type known in the art.

Figure 5:
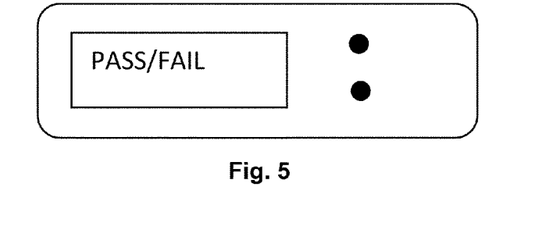
FIG. 5 is a schematic depiction of a test incubator/reader for use in an embodiment of the present invention.
Figure 6:
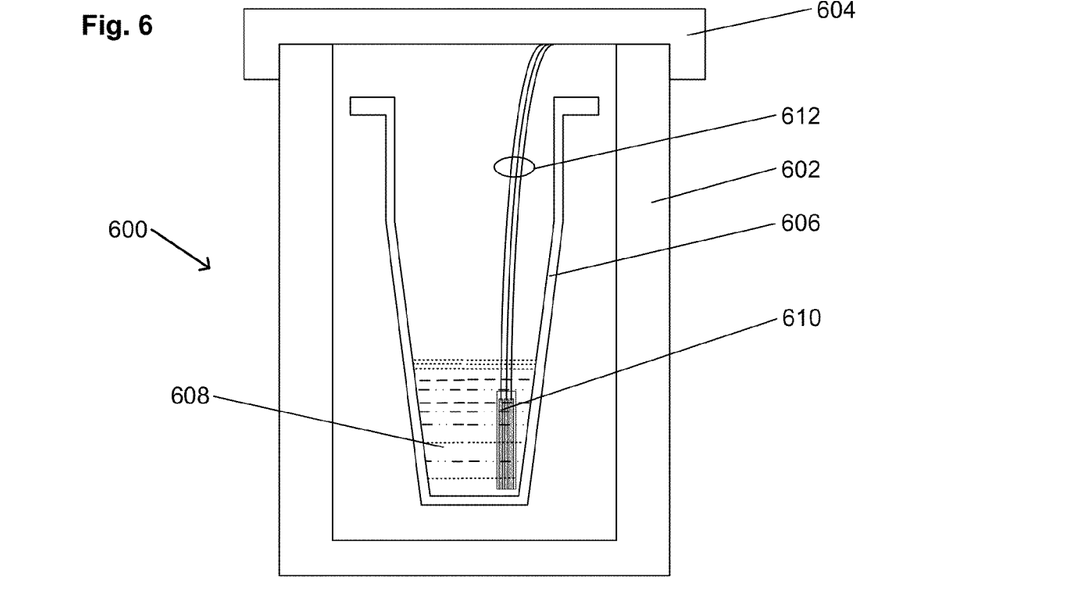
FIG. 6 is a schematic cross-sectional view of an embodiment of a sterilization indicator during incubation with an electro-conductive strip similar to that of FIG. 4 inserted into the growth medium, in a test incubator/reader, in accordance with an embodiment of the present invention.

FIG. 5 is a schematic depiction of a test incubator/reader for use in an embodiment of the present invention. The test incubator/reader may include electrical connections suitable to connect to the three electrodes described with respect to FIG. 4 via one of the connections described. The test incubator/reader may include heating and atmosphere controls to provide an appropriate temperature and atmosphere for incubation of the combined contents of the first compartment and the second compartment of the sterilization indicator. The test incubator/reader may further include electronic circuitry adapted to detect and measure any electrical signal generated when the enzyme provided on the electrodes converts a monosaccharide, e.g., glucose, to reaction products including free electrons, in accordance with the present invention. FIG. 6 provides an example of a suitable arrangement for the test incubator/reader depicted in FIG. 5.

FIG. 6 is a highly schematic cross-sectional view of an exemplary sterilization indicator during incubation in an exemplary test incubator/reader 600, with the strip containing the electrodes in place. The test incubator/reader depicted in FIG. 6 includes a lower container 602 and a cap or lid 604. As shown in FIG. 6, disposed in the test incubator/reader 600 is a sterilization indicator vial 606, in which the recovery/incubation medium 608 has been combined with spores of a selected test organism, e.g., *Geobacillus stearothermophilus*, following a sterilization process which is being subjected to efficacy determination in accordance with an embodiment of the present invention. The test incubator/reader 600 is equipped with an electro-conductive strip 610, similar to that of FIG. 4, which has been inserted into the combined contents of the first and second compartments in the container 602, in the test incubator/reader 600 in accordance with an embodiment of the present invention. The test incubator/reader 600 further includes hard-wired electrical connections 612 between the three electrodes on the strip 610 and the electrical circuitry used to detect any electrical activity generated by the enzymatic conversion of simple sugars to their reaction products. As described with respect to FIG. 4, the test incubator/reader 600 may communicate with the strip 610 via any appropriate method.

FIG. 6 is representative of an embodiment of a vial 606 in which there is only one compartment, e.g., in which the optional first compartment is absent, the spores are disposed on the strip 610, and the strip 610 initially is separate from the second compartment. As shown in FIG. 6, the initially separate strip 610 has been placed into the growth medium 608 which contains one or more of a disaccharide, an oligosaccharide and a polysaccharide capable of conversion to a monosaccharide by any germinating spores of the one or more microorganism, should any of the microorganisms have survived the sterilization process. In the embodiment in which the first compartment is absent, the growth medium 608 is not necessarily subjected to the sterilization process; in this embodiment, it is only necessary that the strip 610, with the spores disposed on it, be subjected to the sterilization conditions. Of course, appropriate steps should be take to assure that the growth medium is free of any microorganisms capable of producing simple sugars from more complex sugars, and thus, it also may be sterilized or subjected to the same sterilization conditions as is the strip.

Figure 7:
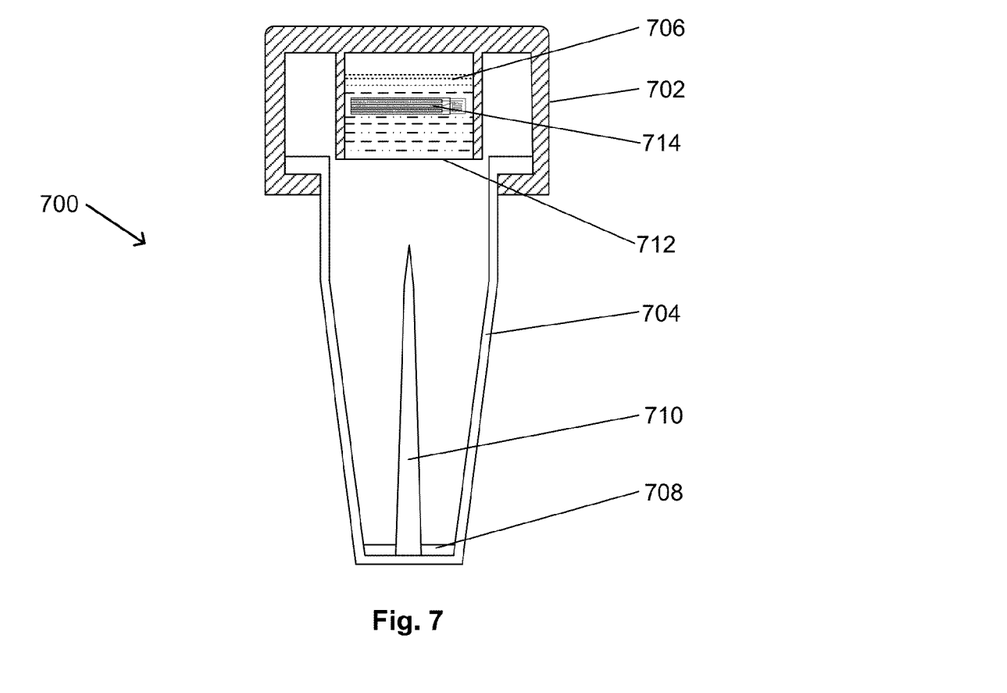
FIG. 7 is a schematic depiction of a sterilization indicator system having a vial in which the spores are in the first compartment and the incubation medium and the strip are in the second compartment, in accordance with an embodiment of the present invention.

FIG. 7 is a schematic depiction of a sterilization indicator system including a vial 700 in which the spores are in the first compartment and the incubation medium and the strip are in the second compartment, in accordance with an embodiment of the present invention. As shown in FIG. 7, the vial 700 includes a cap 702 and a container 704. The container 704 forms a first compartment, and the cap 702 includes a second compartment containing an incubation or recovery medium 706. In the embodiment of FIG. 7, spores of a suitable microorganism are located within the first compartment, and in this embodiment, the spores are immobilized on a carrier 708. The container 704 includes a puncture member 710, which is placed to puncture a breakable barrier 712, when the vial 700 is to be activated for incubation after it has been subjected to a sterilization process. The sterilization indicator system further includes an electro-conductive strip 714 which has two or more electrodes, in this embodiment, three electrodes, which is initially located in the second compartment, i.e., the cap 702. The strip 714 is substantially similar to the strip described above with respect to FIG. 4, but is not limited thereto. As described with respect to FIG. 4, the strip 714 includes suitable electronics to provide a link between the electrodes and an apparatus adapted to detect and measure the electrical signal resulting from electron transfer when any simple sugar present, e.g., glucose, is oxidized by the electrodes. FIG. 7 is an example of an embodiment in which the first compartment is present, the spores are disposed in the first compartment, and the strip initially is in the second compartment.

Figure 8:
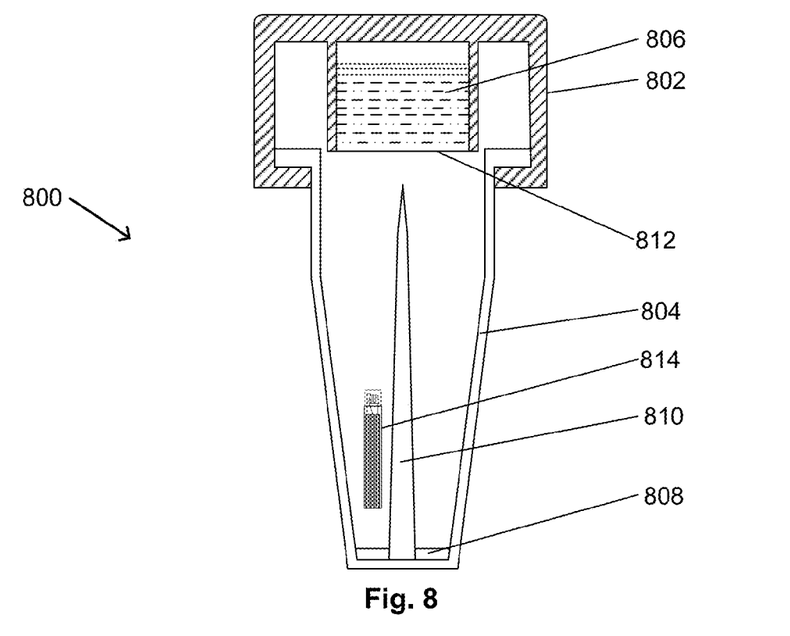
FIG. 8 is a schematic depletion of a sterilization indicator system having a vial in which the spores and the strip are in the first compartment, but are separate from each other, and the incubation medium is in the second compartment, in accordance with an embodiment of the present invention.

FIG. 8 is a schematic depiction of a sterilization indicator system having a vial 800 in which the spores and the strip are in the first compartment, but are separate from each other, and the incubation medium is in the second compartment, in accordance with an embodiment of the present invention. As shown in FIG. 8, the vial 800 includes a cap 802 and a container 804. The container 804 forms a first compartment, and the cap 802 includes a second compartment containing an incubation or recovery medium 806. Spores of a suitable microorganism are located within the first compartment, in one embodiment, the spores are immobilized on a carrier 808. The container 802 includes a puncture member 810, which is placed to puncture a breakable barrier 812, when the vial 800 is to be activated for incubation after it has been subjected to a sterilization process. The sterilization indicator system further includes a strip 814 which has two or more electrodes, in this embodiment, three electrodes, which is located in the first compartment. The strip 814 is substantially similar to the strip described above with respect to FIG. 4, but is not limited thereto. As described with respect to FIG. 4, the strip 814 includes suitable electronics to provide a link between the electrodes and an apparatus adapted to detect and measure the electrical signal resulting from electron transfer when any simple sugar present, e.g., glucose, is oxidized by the electrodes. FIG. 8 is an example of an embodiment in which the first compartment is present, the spores are disposed in the first compartment, and the strip initially is in the first compartment.

Figure 9:
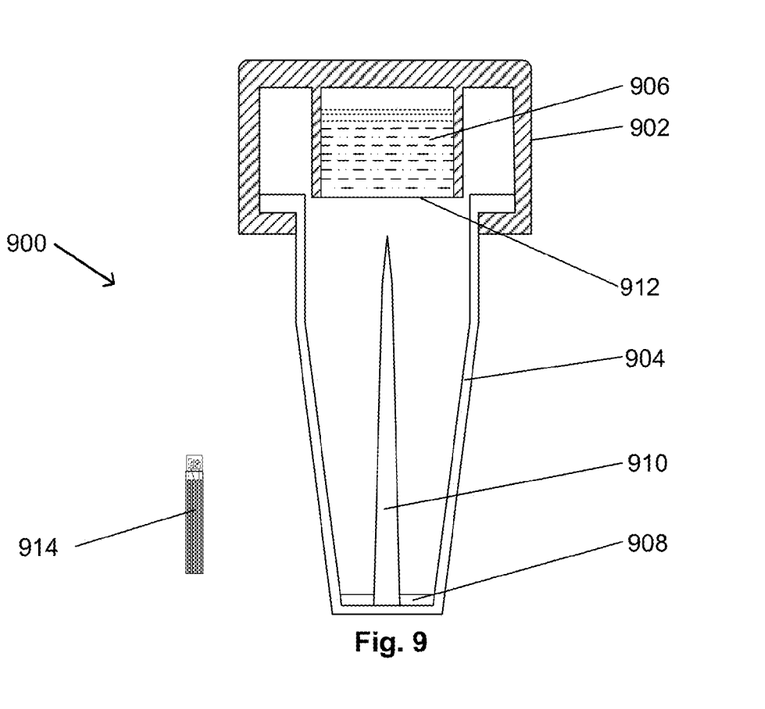
FIG. 9 is a schematic depiction of a sterilization indicator system having a vial in which the spores are in the first compartment and the incubation medium is in the second compartment, and the strip is separate from the vial, in accordance with an embodiment of the present invention.

FIG. 9 is a schematic depiction of a sterilization indicator system having a vial 900 in which the spores are in the first compartment and the incubation medium is in the second compartment, and the strip is separate from the vial, in accordance with an embodiment of the present invention. As shown in FIG. 9, the vial 900 includes a cap 902 and a container 904. The container 804 forms a first compartment, and the cap 902 includes a second compartment containing an incubation or recovery medium 906. Spores of a suitable microorganism are located within the first compartment in one embodiment, the spores are immobilized on a carrier 908. The container 902 includes a puncture member 910, which is placed to puncture a breakable barrier 912, when the vial 900 is to be activated for incubation after it has been subjected to a sterilization process. The sterilization indicator system further includes a strip 914 which has two or more electrodes, in this embodiment, three electrodes, which is located separate from the vial 900. The strip 914 is substantially similar to the strip described above with respect to FIG. 4, but is not limited thereto. As described with respect to FIG. 4, the strip 914 includes suitable electronics to provide a link between the electrodes and an apparatus adapted to detect and measure the electrical signal resulting from electron transfer when any simple sugar present, e.g., glucose, is oxidized by the electrodes. FIG. 8 is an example of an embodiment in which the first compartment is present, the spores are disposed in the first compartment, and the strip initially is separate from both the first compartment and the second compartment.

Figure 10:
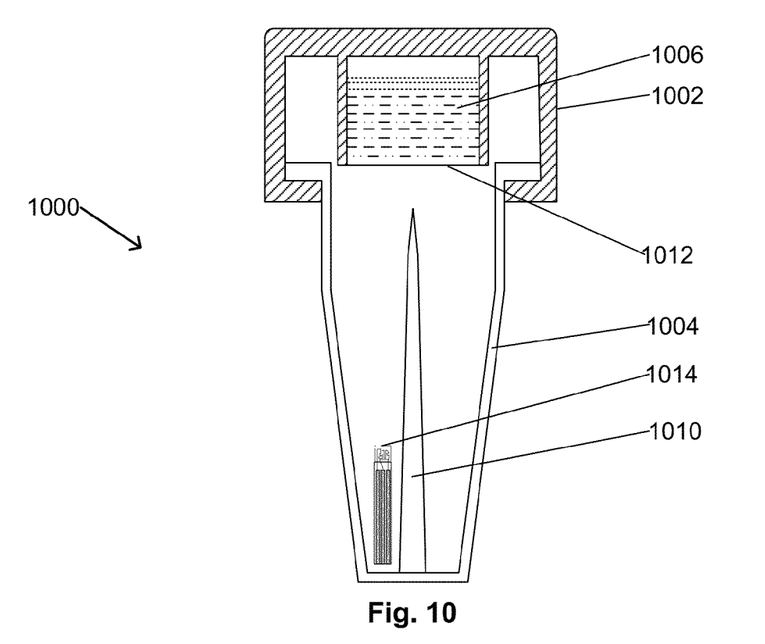
FIG. 10 is a schematic depiction of a sterilization indicator system having a vial in which the spores are on the strip and the strip is in the first compartment, and the incubation medium is in the second compartment, in accordance with an embodiment of the present invention.

FIG. 10 is a schematic depiction of a sterilization indicator system having a vial 1000 in which the spores are on the strip and the strip is in the first compartment, and the incubation medium is in the second compartment, in accordance with an embodiment of the present invention. As shown in FIG. 10, the vial 1000 includes a cap 1002 and a container 1004. The container 1004 forms a first compartment, and the cap 1002 includes a second compartment containing an incubation or recovery medium 1006. Spores of a suitable microorganism are located within the first compartment on a strip 1014, in this embodiment. The container 1002 includes a puncture member 1010, which is placed to puncture a breakable barrier 1012, when the vial 1000 is to be activated for incubation after it has been subjected to a sterilization process. The sterilization indicator system further includes the strip 1014 which has two or more electrodes, in this embodiment, three electrodes, which is located in the first compartment. The strip 1014 is substantially similar to the strip described above with respect to FIG. 4, but is not limited thereto, except that in this embodiment, the strip 1014 also holds the spores. As described with respect to FIG. 4, the strip 1014 includes suitable electronics to provide a link between the electrodes and an apparatus adapted to detect and measure the electrical signal resulting from electron transfer when any simple sugar present, e.g., glucose, is oxidized by the electrodes. FIG. 10 is an example of an embodiment in which the first compartment is present, the spores are disposed on the strip, and the strip initially is in the first compartment.

Figure 11:
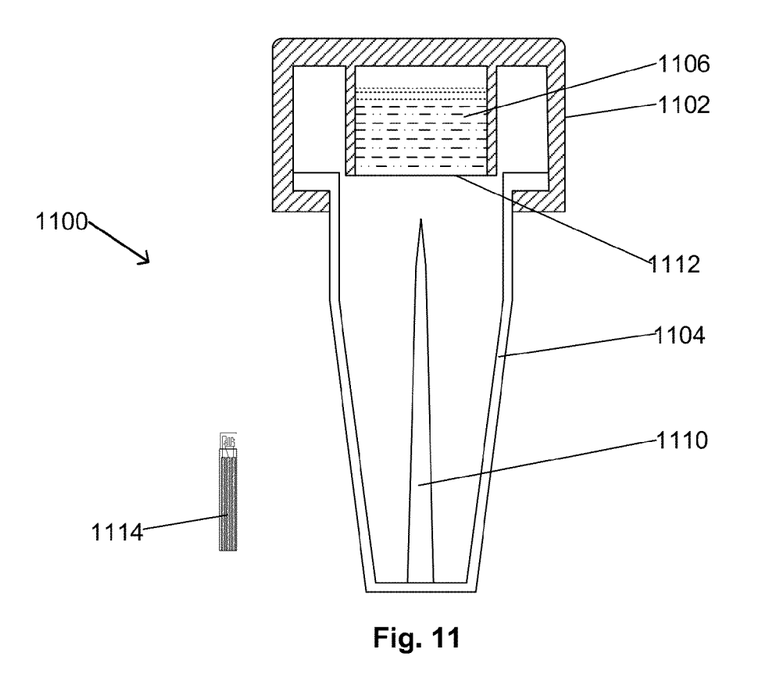
FIG. 11 is a schematic depiction of a sterilization indicator system having a vial in which the spores are on the strip and the strip is separate from the vial, nothing is in the first compartment, and the incubation medium is in the second compartment, in accordance with an embodiment of the present invention.

FIG. 11 is a schematic depiction of a sterilization indicator system having a vial 1100 in which the spores are on the strip and the strip is separate from the vial, nothing is in the first compartment, and the incubation medium is in the second compartment, in accordance with an embodiment of the present invention. As shown in FIG. 11, the vial 1100 includes a cap 1102 and a container 1104. The container 1104 forms a first compartment, and the cap 1102 includes a second compartment containing an incubation or recovery medium 1106. The container 1102 includes a puncture member 1110, which is placed to puncture a breakable barrier 1112, when the vial 1100 is to be activated for incubation after it has been subjected to a sterilization process. The sterilization indicator system further includes a strip 1114 which has two or more electrodes, in this embodiment, three electrodes, which is located separate from the vial 1100. Spores of a suitable microorganism are located on the strip 1114, in this embodiment. The strip 1114 is substantially similar to the strip described above with respect to FIG. 4, but is not limited thereto, except that in this embodiment, the strip 1114 also holds the spores. As described with respect to FIG. 4, the strip 1114 includes suitable electronics to provide a link between the electrodes and an apparatus adapted to detect and measure the electrical signal resulting from electron transfer when any simple sugar present, e.g., glucose, is oxidized by the electrodes. FIG. 11 is an example of an embodiment in which the first compartment is present, the spores are disposed on the strip, and the strip initially is separate from both the first compartment and the second compartment.

Figure 12:
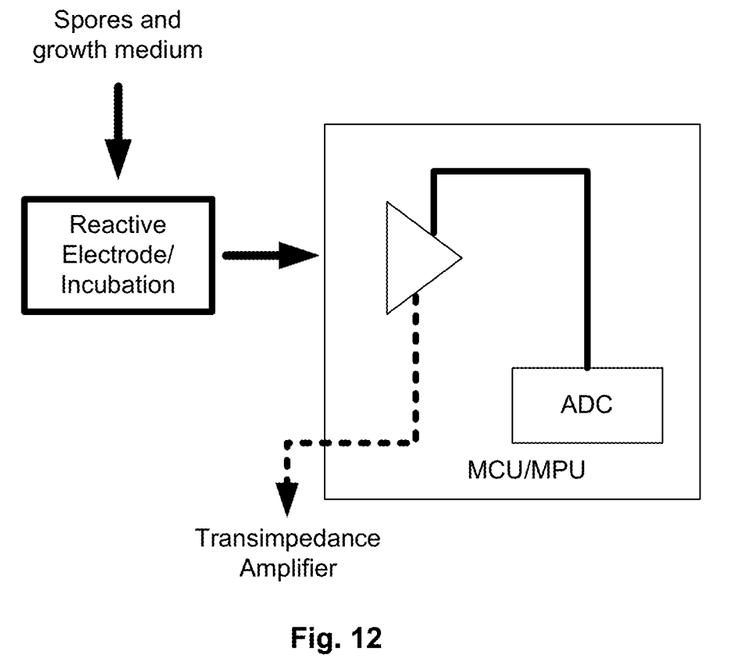
FIG. 12 is a schematic depiction of a device for receiving the signal produced by the reactive electrode, converting it to a digital signal and transferring it to a microcontroller.

FIG. 12 is a schematic depletion of a device for receiving the signal produced by the reactive electrode, converting it to a digital signal and transferring it to a microcontroller. As will be understood by the skilled person, the differential signal obtained from the reactive electrode in the test strip, as modified and measured by the transimpedance amplifier, is fed to an analog digital converter (ADC) and then to the microcontroller/microprocessor unit (MCU/MPU), which in turn outputs the results to a display by which the user can determine the outcome of the test, and whether the sterilization was successful.

Suitable non-enzymatic glucose readers may be selected by those skilled in the art for use with the present invention. Such readers that are commercially available include the Accu-Chek® from Roche Diagnostics, the FreeStyleLite® from Abbott Diabetes Care, and the OneTouch Ultra® from Johnson & Johnson. A laboratory development test system is the EC epsilon electrochemical workstation (Bioanalytical Systems, Inc.). See also, the Electrochemistry Encyclopedia, "Electrochemical Blood Glucose Test Strips for People with Diabetes", Ben Feldman, October, 2009, for additional information on blood glucose readers.

Thus, in one embodiment, the present invention further provides a method for determining the efficacy of a sterilization process. In accordance with this embodiment, the method includes the following steps:

exposing the sterilization indicator system of any preceding claim to a sterilant in a sterilization process;

combining contents of the first compartment and the second compartment, and incubating the combined contents;

contacting the strip with the combined contents before and/or during the incubating and oxidizing any monosaccharide with the two or more electrodes;

linking the apparatus to the two or more electrodes;

with the apparatus linked to the two or more electrodes, detecting and measuring any electrical signal produced by the two or more electrodes from the oxidizing; and determining efficacy of the sterilization process based on the presence or absence of the electrical signal.

The foregoing method can be carried out according to the details provided in the foregoing written description and in conjunction with the knowledge of persons skilled in the art. While some small amount of testing and experimentation may be needed to optimize the production of a suitable sterilization indicator system and the conduction of a suitable sterilization process employing the disclosed sterilization indicator system, any such testing or experimentation will be only minimal.

In the present invention the defection of viable organisms is performed through the monitoring of an electronic signal resulting from the emergence of a simple sugar in a population of germinating spores of the organisms. Only viable spores that have survived the sterilization conditions can express this activity and so appearance of a simple sugar is a positive indicator of viable spores (a FAIL condition when evaluating sterilizer performance). Conversely, the absence of the simple sugar under these test conditions is an indication that no spores in the biological indicator remain viable (a PASS condition for effective sterilizer performance).

In one embodiment, the present invention uses or adapts for use a glucose meter, such as one used for the non-enzymatic determination of blood glucose concentrations for diabetes patients. There is, however, one crucial difference between the present invention and the known use of such glucose meters, and that relates to the concentration of the monosaccharide, e.g., glucose, that is determined. Blood glucose concentrations generally range from about 2 mM (millimolar) to about 30 mM. The concentrations of the monosaccharide, e.g., glucose, determined in accordance with the present invention are much lower, approaching the limits of the existing instrumentation. As is known, the limit of detection when using, for example, CuO nanowire modified electrodes and a fixed potential chronoamperometric method is about 0.0005 mM, or 4 logs lower than standard blood glucose concentrations. As is known, the limit of detection when using molecularly imprinted polymers grafted onto gold electrodes ("MIP Au") is about $2\times10^{-6}$ mM, or 6 logs lower than standard blood glucose concentrations, when using sweeping potential methods of electronic monitoring. The foregoing limits of detection are disclosed in Electrochemical Non-Enzymatic Glucose Sensors: A Perspective and an Evaluation, Kathryn E Toghill and Richard Compton; *Int. J. Electrochem. Sci.*, 5 (2010) 1246-1301. While there are examples of greater sensitivities, the foregoing clearly demonstrates the significant departure of the present invention from existing commercial methods.

In accordance with embodiments of the present invention, the limits of detection of concentrations of the monosaccharide, e.g., glucose, that would indicate the presence of viable, germinating spores that survived the sterilization process are vastly improved over the prior art sterilization indicators and with respect to blood glucose determinations. The improved detection limits provide for much faster determinations of the efficacy of the sterilization process being tested. This is because, should the sterilization process have failed, and spores survived, as the spores begin germinating, the initial concentrations of the monosaccharide will be very low. By enabling the detection of very low concentrations of the monosaccharide, with the present invention, the time delay before any monosaccharide is detected may be reduced to minutes or even seconds, as compared to the hours to days required by conventional sterilization indicators. This represents an important and significant improvement with respect to conventional sterilization indicators.

One factor that may possibly limit the lowest level that can be detected by the present invention is the purity of the disaccharide, oligosaccharide or polysaccharide used in the growth medium. If these higher saccharides are impure and contain significant quantities of the associated monosaccharide, it may be necessary to further purify the disaccharide. Alternatively or in addition, blank samples can be analyzed to determine a baseline, using the same growth medium but without any spores, dead or alive. In such case, the electrical signal resulting from electron transfer when the monosaccharide is oxidized by the electrodes would be that signal that exceeds whatever baseline signal is obtained using the blank samples.

The present invention, in one embodiment, relates to the use of *Geobacillus stearothermophilus* spores, which are the accepted indicator organism for the evaluation of sterilizer cycles using steam and vaporous hydrogen peroxide. The present invention, in another embodiment, relates to the use of *Bacillus atrophaeus* spores, which are the accepted indicator organism for sterilizers using ethylene oxide and dry heat as sterilant. The present invention is unique in the use of an added oligosaccharide (e.g. maltose) as the substrate for naturally occurring, spore associated glycosidase (e.g. alpha-glucosidase) to generate increasing levels of simple sugars, e.g., glucose, as the analyte whose possible emergence from viable spores post-sterilization is monitored in evaluating the efficacy of the relevant sterilization process. The absence of emerging levels of the simple sugar is the indication that the spores of the sterilization indicator are no longer viable and thus evidence of a successful sterilization process. Conversely, the presence of emerging levels of the simple sugar, which is the by-product of viable, germinating spores, is the indication of the failure of the sterilizer to produce the conditions necessary for a successful sterilization. This same process could be used with other spore associated enzymes (e.g., beta-galactosidase) to convert other di-, oligo- or polysaccharides (e.g., lactose) to generate the analyte simple sugar, e.g., glucose. Since the presence of active spore-associated enzymes, or their production after the sterilization event under evaluation, occurs very early in the germination process, the indicator organisms still have all the morphological and membrane properties of spores, although at the point at which the simple sugar is detected, the spores are just beginning to germinate. In a preferred embodiment, the supplemented carbohydrate is maltose which has particular benefits. As the first benefit, the disaccharide does not interact with the electrode to produce a signal without interaction with viable, germinating spores expressing active enzyme, e.g., glucosidase. As another benefit, maltose provides two molecules of glucose rather than one, which is the case for many other potential complex sugars like lactose. One could use other naturally occurring enzymes from the spore like beta-galactosidase and a corresponding substrate like lactose (produces one glucose molecule and one galactose molecule) to achieve the same end—increasing the presence of glucose in the test solution, in either case, the product of the first step (e.g., glucose) would interact with the electrode biosensor of the cited example to produce the detectable signal of the present invention. A third benefit is the ability to use a hand held glucose biosensor for the detection and evaluation of results leading to a PASS or FAIL designation with regard to remaining viable indicator spores. Use of such a biosensor allows for read times of from seconds to minutes which is also new to the field of sterilization cycle monitoring.

An important advantage of the present invention is the faster read time for biological indicators. Additionally, because the signal is measured electronically there is the opportunity for signal conditioning and amplification. Furthermore, with a simple algorithm correlating the direct relationship of oxidizing current to quantity of simple sugar no interpretation of PASS and FAIL will be required by the user. Another advantage over similar technology is that it is independent of any added enzymes that add cost, reduce shelf life and subject the performance of the biological sensor to rate limiting diffusion and enzyme kinetics influences.

The application of non-enzyme glucose detection in blood testing (for which there is a great deal of available data) is influenced by inhibitors found in blood and serum and must be used at physiological conditions including neutral pH. Because these inhibitors are not present in spore preparations used in the sterilization indicator system of the present invention, and because much broader ranges of temperature, pH, ionic strength and other conditions can be used with spores, such conditions can be adjusted to optimize the electrocatalytic needs of the electrode system without regard of the constraints of maintaining physiological conditions. For example, much greater sensitivity can be achieved at values of pH that would not be possible in other enzyme based biological indicator systems.

While the principles of the invention have been explained in relation to certain particular embodiments, these embodiments are provided for purposes of illustration. It is to be understood that various modifications thereof will become apparent to those skilled in the art upon reading the specification. Therefore, it is to be understood that the invention disclosed herein is intended to cover such modifications as fall within the scope of the appended claims. The scope of the invention is limited only by the scope of the claims.

The invention claimed is:

1. A sterilization indicator system, comprising:
   spores of one or more species of microorganism;
   a vial comprising an optional first compartment and a second compartment containing a growth medium comprising one or more of a disaccharide, an oligosaccharide or a polysaccharide capable of conversion to a monosaccharide by germinating spores of the one or more species of microorganism, the vial being adapted to combine contents of the second compartment with the spores for analysis after the vial has been exposed to a sterilant;
   a strip comprising two or more electrodes adapted to oxidize the monosaccharide and to carry an electrical signal resulting from the oxidation of the monosaccharide, wherein the two or more electrodes are adapted to provide contact with the combined contents of the second compartment and the spores during and/or after incubation; and
   an apparatus linked or linkable to the two or more electrodes and adapted to detect and measure the electrical signal resulting from electron transfer when the monosaccharide is oxidized by the two or more electrodes,
   wherein the system is free of the monosaccharide prior to exposure to the sterilant.

2. The sterilization indicator system of claim 1 wherein the first compartment is absent, the spores are disposed on the strip, and the strip initially is separate from the second compartment.

3. The sterilization indicator system of claim 1 wherein the first compartment is present, the spores are disposed on the strip, and the strip initially is separate from both the first compartment and the second compartment.

4. The sterilization indicator system of claim 1 wherein the first compartment is present, the spores are disposed in the first compartment, and the strip initially is separate from both the first compartment and the second compartment.

5. The sterilization indicator system of claim 1 wherein the first compartment is present, the spores are disposed in the first compartment, and the strip initially is in the first compartment.

6. The sterilization indicator system of claim 1 wherein the first compartment is present, the spores are disposed on the strip, and the strip initially is in the first compartment.

7. The sterilization indicator system of claim 1 wherein the first compartment is present, the spores are disposed in the first compartment, and the strip initially is in the second compartment.

8. The sterilization indicator system of claim 1 wherein the monosaccharide is glucose.

9. The sterilization indicator system of claim 1 wherein the one or more species of microorganism comprises one or both of *Geobacillus stearothermophilus* and *Bacillus atrophaeus*.

10. The sterilization indicator system of claim 1 wherein the apparatus is a glucose reader.

11. The sterilization indicator system of claim 1 wherein the two or more electrodes are linkable to a glucose reader by a wireless link.

12. The sterilization indicator system of claim 1 wherein the disaccharide is maltose that is converted to glucose by a glucosidase produced by or present in the germinating spores.

13. The sterilization indicator system of claim 1 wherein the at least two electrodes comprise graphite, graphene, carbon, carbon nanotubes, gold, platinum, palladium, silver, nickel or copper or a combination or alloy of any two or more thereof.

14. A method of determining efficacy of a sterilization process, comprising:
- exposing the sterilization indicator system of claim 1 to a sterilant in a sterilization process;
- combining contents of the first compartment and the second compartment, and incubating the combined contents;
- contacting the strip with the combined contents before and/or during the incubating and oxidizing any monosaccharide with the two or more electrodes;
- linking the apparatus to the two or more electrodes;
- with the apparatus linked to the two or more electrodes, detecting and measuring any electrical signal produced by the two or more electrodes from the oxidizing; and
- determining efficacy of the sterilization process based on the presence or absence of the electrical signal.

* * * * *